(12) United States Patent
Kumar et al.

(10) Patent No.: US 7,977,475 B2
(45) Date of Patent: Jul. 12, 2011

(54) PROCESS FOR THE PREPARATION OF FAROPENEM

(75) Inventors: Neela Praveen Kumar, Hyderabad (IN); Mohan Prasad, Gurgaon (IN)

(73) Assignee: Ranbaxy Laboratories Limited, New Delhi (IN)

( * ) Notice: Subject to any disclaimer, the term of this patent is extended or adjusted under 35 U.S.C. 154(b) by 500 days.

(21) Appl. No.: 12/089,159

(22) PCT Filed: Oct. 5, 2006

(86) PCT No.: PCT/IB2006/053651
§ 371 (c)(1), (2), (4) Date: Jul. 27, 2008

(87) PCT Pub. No.: WO2007/039885
PCT Pub. Date: Apr. 12, 2007

(65) Prior Publication Data
US 2009/0023915 A1    Jan. 22, 2009

(30) Foreign Application Priority Data
Oct. 5, 2005    (IN) .................................. 2676/2005

(51) Int. Cl.
C07D 499/893    (2006.01)
(52) U.S. Cl. ..................................................... 540/310
(58) Field of Classification Search ................. 540/310
See application file for complete search history.

(56) References Cited

U.S. PATENT DOCUMENTS

| | | | |
|---|---|---|---|
| 4,997,829 A | 3/1991 | Ishiguro et al. | 514/192 |
| 5,885,981 A * | 3/1999 | Iwata et al. | 514/195 |
| 7,358,356 B2 * | 4/2008 | Takase et al. | 540/310 |
| 2009/0275746 A1 * | 11/2009 | Parthasaradhi Reddy et al. | 540/310 |

FOREIGN PATENT DOCUMENTS

| | | |
|---|---|---|
| EP | 0 199 446 | 10/1986 |
| EP | 0 410 727 | 1/1991 |
| JP | 4-41489 | 2/1992 |
| JP | 04041489 A * | 2/1992 |

OTHER PUBLICATIONS

T. Nakatsuka and A. Kaneko, Research on the Process of Synthesis of Sodium Salt of Faropenem an Antibiotic of Faropenem, Farumashia (Japanese). (2002) 38(3), pp. 219-223 (and translation).*
Han, Chinese Journal of Pharmaceuticals, 339-341 2001.*
Translation of Han 2001.*
Translation of JP 04041489A.*
second translation of JP04041489 (1992).*

* cited by examiner

Primary Examiner — Mark L Berch

(57) ABSTRACT

The present invention is related to processes for the preparation of faropenem, which comprises treating the compound of Formula II,

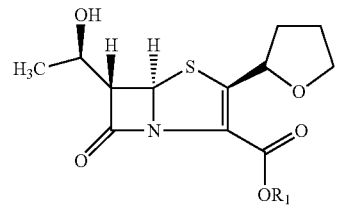

FORMULA II with an alkali metal salt of a substituted or unsubstituted $C_{5-10}$ carboxylic acid and a catalytic amount of a palladium complex in the presence of an organic solvent, followed by the treatment of the reaction mixture of with water and a water miscible solvent, and isolating a hydrate of an alkali metal salt of faropenem from the reaction mass, wherein water is not removed from the reaction mixture in water treatment or isolation steps.

10 Claims, No Drawings

PROCESS FOR THE PREPARATION OF FAROPENEM

FIELD OF THE INVENTION

The present invention is related to processes for the preparation of faropenem.

BACKGROUND OF THE INVENTION (5R,6S)-6-[(1R)-1-hydroxyethyl]-7-oxo-3-[(2R)-tetrahydrofuran-2-yl]-4-thia-1-aza bicyclo[3.2.0]hept-2-ene-2-carboxylic acid, commonly known as faropenem of Formula I is a synthetic, broad-spectrum, carbapenem antibiotic.

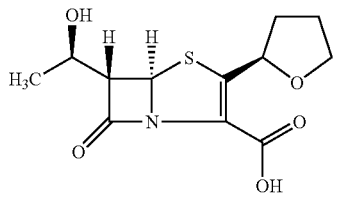

FORMULA I

The sodium salt of faropenem shows potent antibacterial activity against methicillin-sensitive *Staphylococcus aureus* (MSSA), *Streptococcus pyrogenes* and *Streptococcus pneumoniae* and gram-positive bacteria such as penicillin-resistant pneumococci (PRSP), oral *staphylococci* and *enterococci*. It also shows a wide antibacterial spectrum covering gram-negative bacteria such as *Haemophilus influenzae* and anaerobic bacteria such as the genus *Bacteroides*.

U.S. Pat. No 4,997,829 provides a process for the preparation of sodium and potassium salts of faropenem, involving the deprotection of allyl faropenem in the presence of triphenylphosphine, palladium tetrakis-triphenylphosphine and sodium or potassium 2-ethylhexanoate. However, the process disclosed in the '829 patent does not result in stable and commercially useful hydrates of faropenem salts.

EP Patent No. 410,727 provides various processes for preparing the hemipentahydrate of faropenem salts, involving the deprotection of allyl faropenem in the presence of an alkali metal enolate of 1,3-diketone. The faropenem formed in situ is converted into hemipentahydrate by the addition water. JP Patent No 2,949,363 B2 also provides a process for preparing hydrates of faropenem salts by treating deprotected faropenem with an alkali metal salt of a $C_{1-4}$ carboxylic acid in the presence of water.

The water added to the reaction mixture to effect the formation of hydrates in the prior art processes is removed by distillation. However, the removal of water from the reaction mixture under reduced pressure consumes both time and energy. Additionally the solution stability of faropenem sodium in water is very poor and prolonged storage or heating results in impurity formation.

SUMMARY OF THE INVENTION

While working on this problem, the present inventors have developed advantageous processes for the preparation of hydrates of alkali metal salts of faropenem. The present process does not involve the removal of water and it provides the hydrates of faropenem with higher yield, reduced time cycle and greater purity, rendering the process economical and industrially viable.

DETAILED DESCRIPTION OF THE INVENTION

In one aspect, a process for the preparation of a hydrate of an alkali metal salt of faropenem is provided, wherein the process comprises,
a) treating the compound of Formula II,

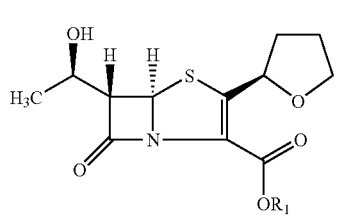

FORMULA II wherein $R_1$ is selected from optionally substituted $C_1$-$C_8$ alkyl, optionally substituted $C_3$-$C_8$ alkenyl, optionally substituted $C_7$-$C_{19}$ aralkyl, or optionally substituted $C_6$-$C_{12}$ aryl, with an alkali metal salt of a substituted or unsubstituted $C_{5-10}$ carboxylic acid and catalytic amount of a palladium complex in the presence of an organic solvent;
b) treating the reaction mixture of step a) with water and a water-miscible solvent; and
c) isolating a hydrate of an alkali metal salt of faropenem from the reaction mass thereof,
wherein water is not removed from the reaction mixture in step b) or c).

The compound of Formula II can be prepared, for example, according to methods provided in the prior art mentioned above. The compound of Formula II can be dissolved in an organic solvent, selected from, for example, dichloromethane, dichloroethane, chloroform, methyl acetate, ethyl acetate, tetrahydrofuran, diethyl ether, methanol, ethanol, acetonitrile, propionitrile, acetone or methyl ethyl ketone. The solution so obtained can be treated with an alkali metal salt of a substituted or unsubstituted $C_{5-10}$ carboxylic acid and catalytic amount of a palladium complex. The $C_{5-10}$ carboxylic acid can be 2-ethylhexanoic acid, pentanoic acid, hexanoic acid or heptanoic acid. The acid can be used in the form of an alkali metal salt or an alkali metal hydroxide together with $C_{5-10}$ carboxylic acid can be used. The palladium complex can be selected from, for example, tetrakis(triphenylphosphine) palladium (O), bis(triphenylphosphine) palladium (II) dichloride, dichloro-di-(benzonitrile palladium (II), or palladium diacetate. The palladium complex can be used together with a phosphine ligand such as triarylphosphine.

Addition of water to the reaction mixture helps in the formation of the hydrates of faropenem salt. Addition of a water-miscible solvent to the reaction mixture facilitates the precipitation of the hydrate. The water-miscible solvent can be selected from, for example, acetone, tetrahydrofuran, methanol, ethanol, isopropyl alcohol, dioxane or acetonitrile. The hydrate of alkali metal salt of faropenem can be isolated from the reaction mixture by filtration.

While the present invention has been described in terms of its specific embodiments, certain modifications and equivalents will be apparent to those skilled in the art and are intended to be included within the scope of the present invention.

EXAMPLE 1

Preparation of Faropenem Sodium Hemipentahydrate

Allyl (5R,6S)-6-[(1R)-1-hydroxyethyl]-7-oxo-3-[(2R)-tetrahydrofuran-2-yl]-4-thia-1-azabicyclo[3.2.0]hept-2-ene- 2-carboxylate (72 g, 0.221 mol) was dissolved in methylene chloride (950 ml). The solution was cooled to 10° C. and triphenyl phosphine (2.0 g, 0.0076 mol), sodium-2-ethylhexanoate (39.71 g, 0.239 mol) and tetrakis triphenylphosphine palladium (0) (2.0 g) were added together at 10° C. The reaction mixture was stirred for 1-2 hours at 10-15° C. After the completion of reaction, water (50 ml) was added to the reaction mixture. The reaction mixture was stirred for 15 minutes, followed by the addition of acetone (332.5 ml) and the reaction mixture was cooled to 0° C. The solid so separated from the reaction mixture was filtered, washed with acetone and dried under reduced pressure to obtain the title compound.

Yield: 64 g; Purity by HPLC: 99.0%.

The invention claimed is:

1. A process for the preparation of a hydrate of an alkali metal salt of faropenem, wherein the process comprises, a) treating the compound of Formula II,

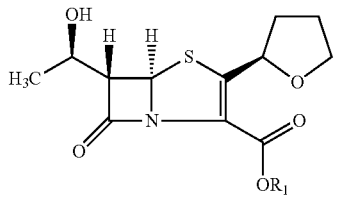

FORMULA II wherein $R_1$ is $C_1$-$C_8$ alkyl, $C_3$-$C_8$ alkenyl, $C_7$-$C_{19}$ aralkyl, or $C_6$-$C_{12}$ aryl, with an alkali metal salt of a substituted or unsubstituted $C_{5-10}$ carboxylic acid and a catalytic amount of a palladium complex in the presence of an organic solvent;

b) treating the reaction mixture of step a) with water and a water miscible solvent, c) isolating a hydrate of an alkali metal salt of faropenem from the reaction mass thereof, wherein water is not removed from the reaction mixture in step b) or c).

2. The process as claimed in claim 1, wherein the hydrate of an alkali metal salt of faropenem is faropenem sodium hemipentahydrate.

3. The process as claimed in claim 1, wherein the $C_{5-10}$ carboxylic acid is 2-ethylhexanoic acid.

4. The process as claimed in claim 1, wherein the palladium complex is selected from tetrakis(triphenylphosphine) palladium (0), bis(triphenylphosphine) palladium (II) dichloride, dichloro-di-(benzonitrile palladium (II), or palladium diacetate.

5. The process as claimed in claim 4, wherein the palladium complex is tetrakis(triphenylphosphine) palladium (0).

6. The process as claimed in claim 1, wherein the organic solvent is selected from dichloromethane, dichloroethane, chloroform, methyl acetate, ethyl acetate, tetrahydrofuran, diethyl ether, methanol, ethanol, acetonitrile, propionitrile, acetone or methyl ethyl ketone.

7. The process as claimed in claim 1, wherein the palladium complex is used along with a phosphine ligand.

8. The process as claimed in claim 7, wherein the phosphine ligand is triaryl phosphine.

9. The process as claimed in claim 1, wherein the water-miscible solvent is selected from acetone, tetrahydrofuran, methanol, ethanol, isopropyl alcohol, dioxane or acetonitrile.

10. The process as claimed in claim 9, wherein the water-miscible solvent is acetone.

* * * * *